United States Patent
Liang et al.

(10) Patent No.: US 7,575,715 B2
(45) Date of Patent: Aug. 18, 2009

(54) METHODS FOR STERILIZING MEDICAL DEVICES USING A HYDROGEN SURFACE-MIXED DIFFUSION FLAME

(75) Inventors: David Tee Liang, Singapore (SG); Joo Hwa Tay, Singapore (SG); Tuti Mariana Lim, Singapore (SG); Dong Fei Li, Singapore (SG)

(73) Assignee: Nanyang Technological University, Singapore (SG)

( * ) Notice: Subject to any disclaimer, the term of this patent is extended or adjusted under 35 U.S.C. 154(b) by 149 days.

(21) Appl. No.: 10/558,102

(22) PCT Filed: May 22, 2003

(86) PCT No.: PCT/SG03/00122

§ 371 (c)(1),
(2), (4) Date: Oct. 27, 2006

(87) PCT Pub. No.: WO2004/103417

PCT Pub. Date: Dec. 2, 2004

(65) Prior Publication Data

US 2007/0172384 A1 Jul. 26, 2007

(51) Int. Cl.
*A61L 2/20* (2006.01)
(52) U.S. Cl. .......................... 422/28; 422/38

(58) Field of Classification Search .................. 422/23, 422/28, 38, 292, 307
See application file for complete search history.

(56) References Cited

U.S. PATENT DOCUMENTS

| | | | | |
|---|---|---|---|---|
| 4,552,728 | A | * | 11/1985 | Taylor .......................... 422/300 |
| 4,892,705 | A | | 1/1990 | Sternfeld et al. |
| 5,314,847 | A | | 5/1994 | Watanabe et al. |
| 6,267,585 | B1 | * | 7/2001 | Suttrop ........................ 431/354 |

FOREIGN PATENT DOCUMENTS

| | | |
|---|---|---|
| EP | 0780631 | 6/1997 |
| WO | WO 03/043751 | 5/2003 |

* cited by examiner

*Primary Examiner*—Sean E Conley
(74) *Attorney, Agent, or Firm*—Blakely, Sokoloff, Taylor & Zafman LLP

(57) ABSTRACT

A method for sterilizing medical devices, comprising the steps: producing a plurality of hydrogen surface-mixed diffusion flame; exposing the plurality of hydrogen surface-mixed diffusion flame to the medical devices for a predetermined period of time; and exposing the medical devices to the plurality of hydrogen surface-mixed diffusion flame at a predetermined distance; wherein the hydrogen surface mixed diffusion flame further produces free radicals for further sterilizing of the medical devices.

18 Claims, 3 Drawing Sheets

METHODS FOR STERILIZING MEDICAL DEVICES USING A HYDROGEN SURFACE-MIXED DIFFUSION FLAME

CROSS-REFFERENCE TO OTHER APPLICATIONS

This is a National Phase of International Application No. PCT/SG2003/000122, filed on May 22, 2003.

FIELD OF THE INVENTION

The present invention relates in general to an apparatus and method for sterilizing medical and laboratory instrument and devices. More particularly, the invention relates to an apparatus and method for using a cool hydrogen flame for sterilizing medical and laboratory instrument and devices.

BACKGROUND OF THE INVENTION

Several million surgical procedures are performed every year on patients in hospitals and medical facilities all over the world. This does not include the other several million procedures performed by dental professionals on their patients. A major risk in all such invasive procedures is that of introducing infection. One of the most common ways of introducing infection is the failure to properly and sufficiently sterilize the surgical instruments or devices used in these procedures.

Use of disposal medical instruments have been viewed to be an essential step in this prevention of infection. However, even disposal medical instruments must first be sterilized before being packed into their sterile packagings.

Several sterilization technologies have been developed and are currently in use in a variety of systems all over the world. One of the most popular and traditional methods of sterilization is known as autoclave steam sterilization. It is considered highly effective, economical and does not present a source of danger to humans during the sterilization process. Furthermore, it is easily controllable and produces no dangerous by-products. However, the limitations of autoclave steam sterilization lie in its use of steam which exposes the devices being sterilized to high temperatures in excess of 100° C. as well as the introduction of moisture. In situations where medical instruments are not made to good specifications, exposure to this high temperature and moisture may well cause them to deteriorate or to even rust.

Other technologies developed for such sterilization purposes are ethylene oxide gas sterilization, gamma radiation sterilization, and hydrogen peroxide gas plasma sterilization. Each of these sterilization technologies have their own limitations that prevent their wide spread use and replacement of autoclave steam sterilization.

Ethylene oxide gas sterilization is costly and by-products and residues are toxic and require additional systems for their safe removals. Gamma radiation sterilization is also costly and the frequent exposure to radiation is also dangerous to humans and may potentially cause damage to the medical instruments. Hydrogen peroxide gas plasma is also costly and requires special packaging and container trays.

A new type of sterilization technology uses Ozone gas as a powerful oxidant to decompose into secondary oxidants which are highly reactive and capable of destroying microorganisms. However, the reactive nature of Ozone gas prevents its wide spread use as it poses a risk in degradation of the materials of the instruments being sterilized.

There is thus at present a glaring lack for an apparatus and method for sterilizing of medical and laboratory instruments and devices without the limitations of costs, safety and by-products.

SUMMARY OF THE INVENTION

The present invention seeks to provide a method and apparatus for sterilizing of medical and laboratory instruments and devices.

Accordingly, in one aspect, the present invention provides, a method for sterilizing medical devices, comprising the steps: producing a plurality of hydrogen surface-mixed diffusion flame; exposing the plurality of hydrogen surface-mixed diffusion flame to the medical devices for a predetermined period of time; and exposing the medical devices to the plurality of hydrogen surface-mixed diffusion flame at a predetermined distance; wherein the hydrogen surface mixed diffusion flame further produces free radicals for further sterilizing of the medical devices.

In another aspect, the present invention provides, a method for sterilizing medical devices in a sterilization chamber having placement means and a plurality of burner nozzles, comprising the steps: mounting instruments on the placement means within the sterilization chamber; igniting the plurality of burner nozzles to introduce a plurality of configurable hydrogen surface-mixed diffusion flame into the sterilization chamber; controlling the plurality of configurable hydrogen surface mixed-diffusion flame; exposing the medical devices to the plurality of configurable hydrogen surface-mixed diffusion flame for a predetermined period of time; and exposing the medical devices to the plurality of configurable hydrogen surface-mixed diffusion flame at a predetermined distance.

In a further aspect, the present invention provides, an apparatus for sterilizing medical devices comprising: a sterilizing chamber; a placement means for placing of the medical devices in the sterilizing chamber, and a plurality of burner nozzles for producing a plurality of configurable hydrogen surface-mixed diffusion flame.

BRIEF DESCRIPTION OF THE DRAWINGS

A preferred embodiment of the present invention will now be more fully described, with reference to the drawings of which.

DETAILED DESCRIPTION OF THE DRAWINGS

In this description, an apparatus and method for sterilizing medical and laboratory instruments and devices. In the following description, details are provided to describe the preferred embodiment. It shall be apparent to one skilled in the art, however that the invention may be practiced without such details. Some of the details may not be described at length so as not to obscure the invention.

Figure 1:
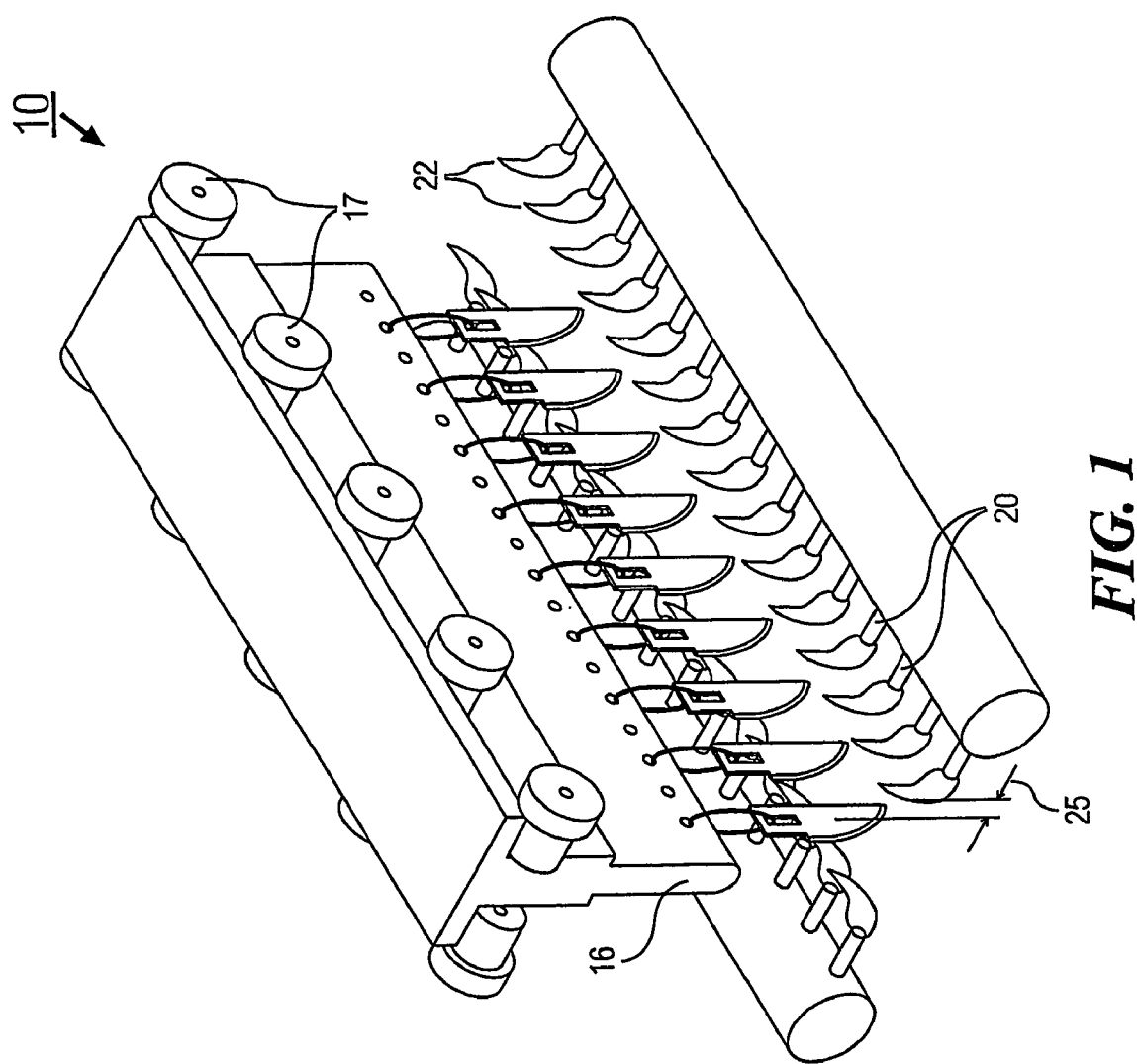
FIG.1 illustrates an apparatus in accordance with the present invention.

Referring to FIG. 1, an apparatus for sterilizing medical and laboratory instruments and devices is illustrated. The apparatus 10 comprises of a sterilizing chamber, a vacuum pump, a placement means, and a plurality of burner nozzles 20 producing a plurality of configurable hydrogen surface-mixed diffusion flame 22. The placement means and the plurality of burner nozzles are disposed in the steriizing chamber. The vacuum pump is used to keep the pressure inside the sterilizing chamber lower than that of atmospheric pressure and serves as a safety feature to carry away unburnt gases. The vacuum pump also serves to carry away any debris or by-products from the sterilization of the medical and laboratory instruments and devices.

During operation, medical, laboratory instruments and devices (hereafter referred to as medical devices 30) are placed on placement means inside the sterilizing chamber. The plurality of burner nozzles 20 are ignited to generate a plurality of configurable hydrogen surface-mixed diffusion flames (CHSMDFs) 22. The flames produced from these burner nozzles 20 can be described to be gentle, "cool" and clean burning. The plurality of CHSMDF 22 are produced by burning pure hydrogen in either pure oxygen or purified air with or without oxygen enrichment. However, the hydrogen and oxygen are not pre-mixed before being ignited. Instead, the burner nozzle 20 may be of a tube in orifice design That is to say, a main nozzle ejecting oxygen gas, and a central nozzle positioned inside the main nozzle ejecting hydrogen gas. When the burner nozzle 20 is in operation, hydrogen gas is being ejected with an envelope of oxygen gas surrounding it. When this hydrogen gas is ignited, it burns only at the envelope of the hydrogen gas and oxygen gas interface. This produces a flame referred to as a configurable surface-mixed diffusion flame (CHSMDF) 22. It can be described as a "cool" burning flame as its temperature is much lower than the conventional pre-mixed flames. The burner nozzles may not necessarily be limited to the tube in orifice design and may also comprise a slot type burner nozzle.

To ensure complete combustion of the hydrogen gas, an excess of oxygen is ejected from the burner nozzles 20. Since the sterilizing chamber 12 is operating at about below atmospheric pressure, there is no opportunity for unburnt gases to accumulate and pose a danger.

Using flames for the sterilization of medical devices 30 is by no means new. However, conventional flames using hydrocarbon fuels are simply too "dirty" for reliable use in sterilization procedures. Conventional flames would produce soot that would contaminate the medical devices 30. Further, the high temperatures produced by conventional flames may not be suitable for certain medical devices 30 that are not made of metal. Only the hydrogen surface mixed diffusion flame is "cool" enough to be used to sterilize and destroy microorganisms on such medical devices 30. The clean-burning of hydrogen flames does not produce soot or carbon particles. The absence of soot during combustion also significantly reduces radiative heat release by hydrogen flames thus making it a "cool" flame. The main by-product from this hydrogen flame is water and free radicals.

These free radicals produced during hydrogen combustion are extremely reactive and highly oxidative in nature especially hydroxyl radicals. Some of the hydrogen and oxygen gases being burnt will be converted into these free radicals. These free radicals are capable of interacting with essential cell components (e.g. enzymes and nucleic acids) and thereby disrupt the metabolism of microorganisms or essentially inactivate them. This effectively also provides a means of sterilizing the medical devices 30 inside the sterilizing chamber.

Referring to FIG. 1, one example of the placement means is a hanging frame 16 for hanging the medical devices 30 to be sterilized inside the sterilizing chamber 12. The hanging frame 16 can be a plurality of overhanging rails or a frame with hanging means such as hooks and loops for the hanging of the medical devices 30. The hanging frame 16 is movable and by moving the medical devices back and forth or in a predetermined manner, allows the CHSMDF 22 to "gently" sweep over the medical devices 30 sterilizing them with the flames and also with the free radicals produced by the CHSMDF 22. Alternatively, the hanging frame 16 may remain stationery while the CHSMDF 22 are moved and swept over the medical devices 30 instead.

Figure 2:
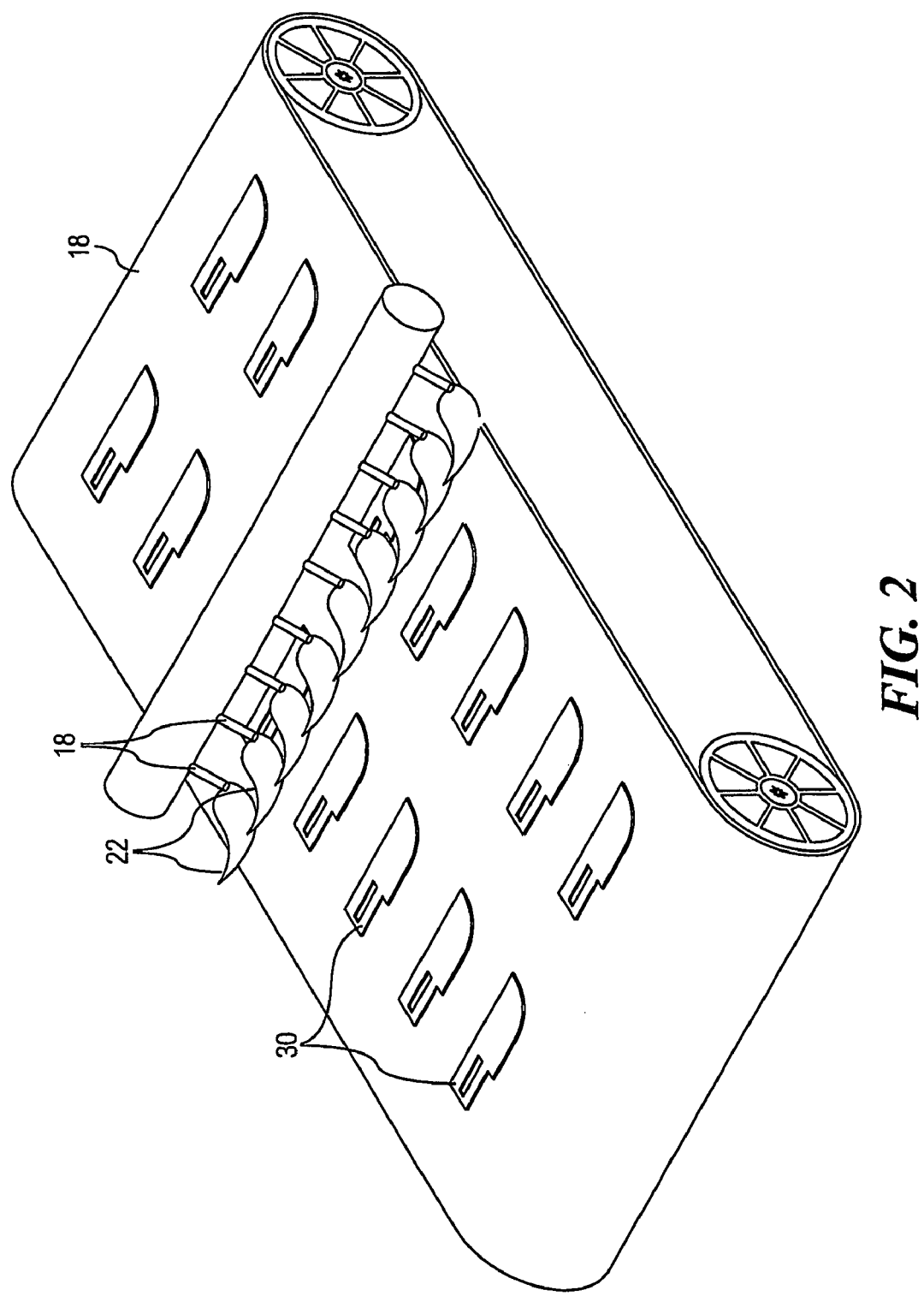
FIG.2 illustrates an alternative placement means of FIG.1.

Referring to FIG. 2, an alternative placement means can be a placement conveyor 18 made of metal mesh allowing direct access to the medical devices 30 placed on the placement rack 18 from both above and below. The placement conveyor 18 allows the medical devices 30 to be moved in a back and forth motion, thus allowing the CHSMDF 22 to "gently" sweep over the medical devices 30 on the placement conveyor 18.

Alternatively, the placement means such as the hanging frame 16 and the placement conveyor 18 may be immobile and the plurality of burner nozzles 20 may be movable providing the sweeping motions for the CHSMDF 22.

Yet another alternative would be the combination of both the burner nozzles 20 and the placement means being movable.

Other alternatives to the placement means may be metal racks allowing placement of medical devices 30 on the rack where the CHSMDF 22 will have access to both the top and the bottom of the medical devices 30.

Many medical devices are invariably made of stainless steel or metal and have a high tolerance for heat and may be exposed directly to the CHSMDF 22. However, some medical devices 30 are not made of metal and have low tolerance for heat. When dealing with such medical devices 30 having low tolerances for heat, the plurality of CHSMDF 22 produced by the burner nozzles have to be controlled or configured. The flame throw of the plurality of CHSMDF 22 is shortened until a deadspace 25 is formed in the sterilizing chamber 12. This deadspace 25 is a predetermined three dimensional space in the sterilizing chamber which does not come into direct contact with the plurality of CHSMDF 22. Thus the temperature in this deadspace 25 is relatively lower than that of the CHSMDF 22. However, the deadspace 25 is still highly concentrated with free radicals produced by the CHSMDF 22. Thus, medical devices 30 that have low temperature tolerances can still be sterilized by placing them in this deadspace 25

Figure 3:
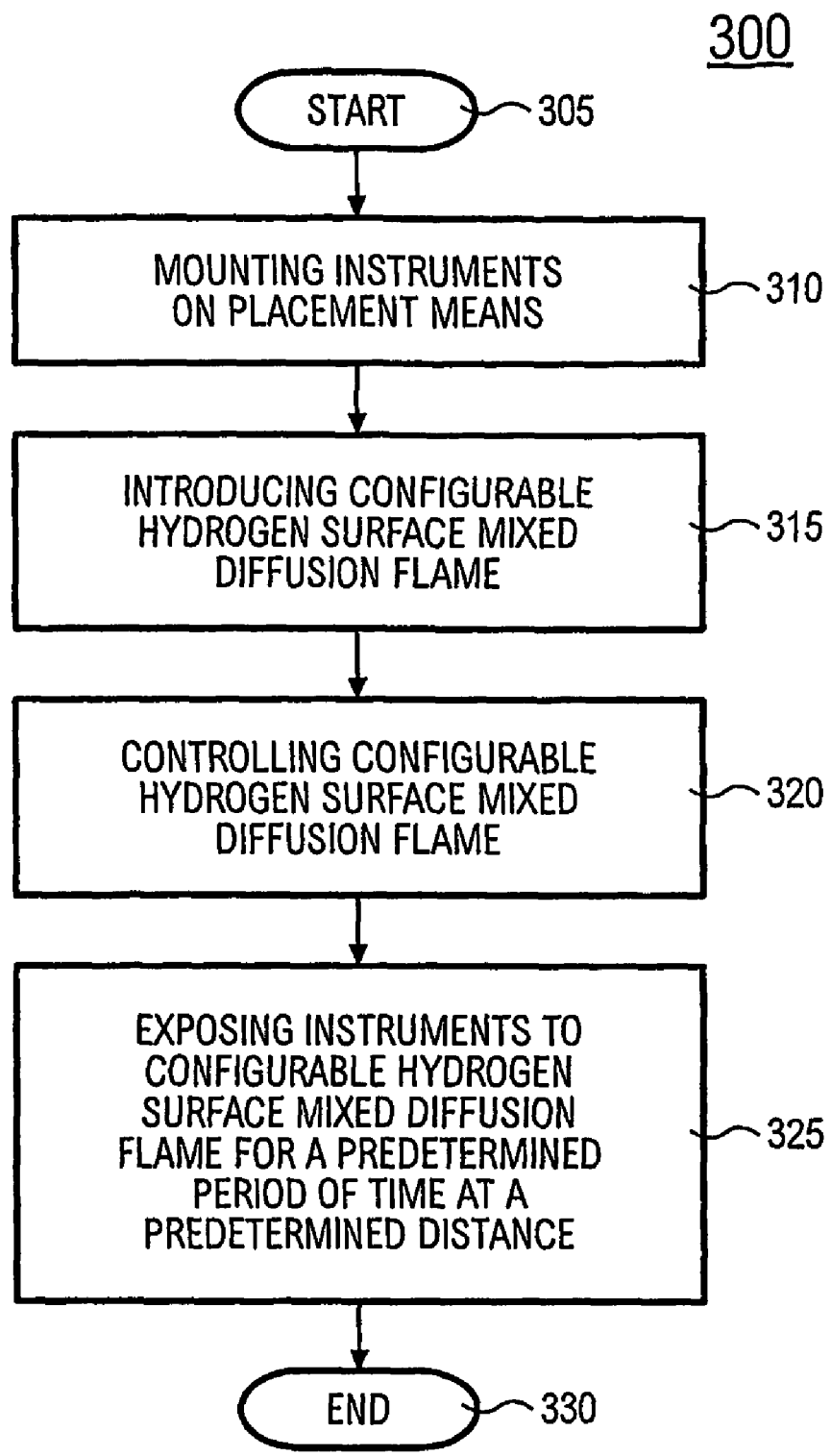
FIG.3 illustrates a flowchart of a method in accordance with the present invention.

Referring to FIG. 3, the method 300 in accordance with the present invention for sterilizing medical instruments and devices is illustrated. The method 300 starts with the mounting 310 of the medical devices 30 on the placement means. When the placement means is a hanging frame 16, the medical devices 30 are mounted onto the hanging frame by hanging from hooks or hanging loops. Next, the plurality of CHSMDF 22 are introduced 315 and the plurality of CHSMDF 22 controlled 320 to lengthen and shorten the flame throw. This is to create or form the deadspace 25 so that medical devices 30 with low tolerance for heat may still undergo sterilization. The plurality of CHSMDF 22 may also be controlled such that the flame throw comes into direct contact with the medical devices 30 when the medical devices 30 being sterilized have high tolerance to heat.

The medical devices 30 are then exposed 325 to the CHSMDF 22 for a predetermined period of time and at a predetermined distance(i.e. direct contact or deadspace) depending on the medical devices' tolerance for heat. The plurality of CHSMDF 22 may be swept gently onto the medical devices 30 in a predetermined manner to further enhance the exposure of the flames to the medical devices 30.

The production of free radicals by hydrogen combustion which is important to the present invention can further be enhanced by addition of certain predetermined chemical agents or modifiers. Examples of such chemical agents are ozone gas and hydrogen peroxide. The apparatus 10 of the present invention can further comprise a plurality of gas nozzles and a plurality of spray nozzles for the introduction of ozone gas or hydrogen peroxide into the sterilizing chamber to enhance the production of free radicals.

Hydrogen peroxide is introduced into the sterilizing chamber in the from of a fine mist by a plurality of spray nozzles. The spray nozzles are preferably located near the plurality of burner nozzles 20 and oriented such that the spray nozzles are pointing at the medical devices 30 being sterilized. The spray nozzles could also be arranged such that the spray nozzles are co-axial to the plurality of burner nozzles 20. The fine mist of hydrogen peroxide directed at the medical devices 30 being sterilized results in more free radicals being formed as the hydrogen peroxide dissociates due to the heat generated by the CHSMDF 22. Any water formed as a result of the dissociation of the hydrogen peroxide is converted into steam by the CHSMDF 22 and removed by the vacuum pump. Correspondingly, the method 300 in accordance with the present invention further comprises an additional step of spraying a fine mist of hydrogen peroxide directed at the medical devices 30. This spraying of fine mist of hydrogen peroxide occurs simultaneously with the sterilization of medical devices 30 using the CHSMDF 22.

Ozone gas is introduced into the sterilizing chamber to enhance the performance of the present invention. The ozone gas is introduced into the sterilizing chamber via a plurality of gas nozzles. The gas nozzles would be sited away from the CHSMDF but directed towards the medical devices 30 after the medical devices 30 have undergone the sterilization by the CHSMDF 22. The introduced ozone dissociates to form oxygen radicals and oxygen gas. These radicals aid further in the elimination of any remaining contaminants on the medical devices 30. Furthermore, the method 300 in accordance to the present invention would further comprise an additional step of directing ozone gas at the medical devices 30.

It will be appreciated that various modifications and improvements can be made by a person skilled in the art without departing from the scope of the present invention.

The invention claimed is:

1. A method for sterilizing medical devices, comprising the steps: a. producing a plurality of hydrogen surface-mixed diffusion flame; and b. exposing said plurality of hydrogen surface-mixed diffusion flame to said medical devices for a predetermined period of time; wherein said hydrogen surface mixed diffusion flame further produces free radicals for further sterilizing of said medical devices.

2. The method according to claim 1, wherein said method is performed in a vacuum environment.

3. The method according to claim 1, wherein said plurality of hydrogen surface-mixed diffusion flame is configurable.

4. The method according to claim 3, further comprising the step: c. exposing said plurality of hydrogen surface mixed diffusion flame to said medical devices at a predetermined distance.

5. The method according to claim 4 wherein said predetermined distance depends on heat tolerance of said medical devices.

6. The method according to claim 1, wherein said hydrogen surface-mixed diffusion flame is produced by burning pure hydrogen in pure oxygen without pre-mixing.

7. The method according to claim 6, wherein said pure oxygen is in excess of said pure hydrogen.

8. The method according to claim 4, further comprising the step: d. spraying a fine mist of hydrogen peroxide towards said hydrogen surface-mixed diffusion flame and said medical devices.

9. The method according to claim 4, further comprising the step: e. directing ozone gas at said medical devices.

10. A method for sterilizing medical devices in a sterilization chamber having placement means and a plurality of burner nozzles, comprising the steps a. mounting instruments on said placement means within said sterilization chamber, b. igniting said plurality of burner nozzles to introduce a plurality of configurable hydrogen surface-mixed diffusion flame into said sterilization chamber; c. controlling said plurality of configurable hydrogen surface-mixed diffusion flame; and d. exposing said medical devices to said plurality of configurable hydrogen surface-mixed diffusion flame for a predetermined period of time.

11. The method according to claim 10, wherein said method is performed in a vacuum environment.

12. The method according to claim 10, further comprising the step: e. exposing said medical devices to said plurality of configurable hydrogen surface-mixed diffusion flame at a predetermined distance.

13. The method according to claim 12, wherein said predetermined distance depends on heat tolerance of said medical devices.

14. The method according to claim 10, wherein said configurable hydrogen surface-mixed diffusion flame is produced by burning pure hydrogen in pure oxygen without pre-mixing.

15. The method according to claim 14, wherein said pure oxygen is in excess of said pure hydrogen.

16. The method according to claim 10, wherein said plurality of burner nozzle are of the tube in orifice in design.

17. The method according to claim 12, further comprising the step: f. spraying a fine mist of hydrogen peroxide towards said plurality of configurable hydrogen surface-mixed diffusion flame and said medical devices.

18. The method according to claim 12, further comprising the step: directing ozone gas at said medical devices.

* * * * *